United States Patent
Imas et al.

(10) Patent No.: US 8,682,051 B2
(45) Date of Patent: Mar. 25, 2014

(54) SMOOTHING OF DYNAMIC DATA SETS

(75) Inventors: Olga Imas, Milwaukee, WI (US); Paul Licato, Wauwatosa, WI (US); Laurent Launay, St Remy Chevreuse (FR); Saad Sirohey, Pewaukee, WI (US); Thierry Galas, Buc (FR); Vincent Adam, Buc (FR)

(73) Assignee: General Electric Company, Schenectady, NY (US)

( * ) Notice: Subject to any disclaimer, the term of this patent is extended or adjusted under 35 U.S.C. 154(b) by 1006 days.

(21) Appl. No.: 12/324,743

(22) Filed: Nov. 26, 2008

(65) Prior Publication Data

US 2010/0128841 A1 May 27, 2010

(51) Int. Cl.
*G06K 9/00* (2006.01)
*G06K 9/32* (2006.01)
*G06K 9/40* (2006.01)

(52) U.S. Cl.
USPC .......................... 382/131; 382/294; 382/264

(58) Field of Classification Search
USPC ................... 382/131, 294, 296, 264
See application file for complete search history.

(56) References Cited

U.S. PATENT DOCUMENTS

| | | | | |
|---|---|---|---|---|
| 5,832,103 | A * | 11/1998 | Giger et al. | 382/130 |
| 6,463,167 | B1 * | 10/2002 | Feldman et al. | 382/128 |
| 6,931,094 | B2 | 8/2005 | Li | |
| 7,912,269 | B2 * | 3/2011 | Ikeda et al. | 382/131 |
| 2005/0018892 | A1 * | 1/2005 | Pieper et al. | 382/131 |
| 2005/0201604 | A1 * | 9/2005 | Hristov | 382/131 |
| 2007/0129627 | A1 | 6/2007 | Profio et al. | |
| 2007/0165943 | A1 * | 7/2007 | Guetter et al. | 382/159 |
| 2009/0185730 | A1 * | 7/2009 | Baumgart et al. | 382/130 |

OTHER PUBLICATIONS

Young, Ian T. et al., Fundamentals of Image Processing, Cover page, title page, and pp. 54-61 (Delft University of Technology, The Netherlands, 1998).
Licato, Paul et al., U.S. Appl. No. 12/324,106, filed Nov. 26, 2008; entitled "System and Method for Automated Diagnosis".

* cited by examiner

*Primary Examiner* — William C Dowling
*Assistant Examiner* — Ryan Howard

(57) ABSTRACT

A data processing technique is provided. In one embodiment, a computer-implemented method includes receiving a set of dynamic computed tomography image data from a computed tomography imaging system, registering the image data, applying a smoothing filter to at least a selection of the registered image data, and outputting the results. The smoothing filter may be, for example, a uniform filter, a triangular filter, a Gaussian filter, a median filter, a percentile filter, a Kuwahara filter, an anisotropic filter, or any combination thereof. Additional methods, systems, and devices are also disclosed.

13 Claims, 4 Drawing Sheets

SMOOTHING OF DYNAMIC DATA SETS

BACKGROUND

The invention relates generally to the field of medical data processing and, more specifically, to techniques for smoothing of dynamic image data sets.

Computed tomography (CT) is an imaging technology commonly used to diagnose diseases internal to the human body. To diagnose acute stroke, for example, medical staff may employ a series of distinct CT examinations, such as non-contrast CT (NCT), CT angiography (CTA), and/or CT perfusion. Generally, a CT perfusion examination may involve providing an iodine contrast in a patient's bloodstream and continuously imaging the patient, typically for around 30-60 seconds with photos captured every 1-3 seconds. A data set resulting from a CT perfusion examination has historically enabled assessment of cerebral ischemic regions. In contrast, NCT has been used to rule out cerebral hemorrhage, while CTA has been used to rule out a brain aneurysm.

Recently, new CT imaging techniques such as Volume Shuttle and Helical Shuttle have expanded the capabilities of CT perfusion. The new techniques may enable extraction of both NCT and CTA data from a single CT perfusion examination, potentially eliminating separate NCT and CTA examinations. CT perfusion examinations may provide further benefits, as dynamic (4D) review of CT perfusion data may enable visualization and assessment of the flow of contrast agent through vasculature of interest, as well as provide differentiation between arterial and venous phases.

Certain limitations to CT perfusion remain. For example, in some cases, spatial resolution and overall quality of CT perfusion data sets may be worse than static data sets, and partial-volume artifacts may be unavoidable. Moreover, the 4D visualization of dynamic CT perfusion data may suffer from temporal sampling limitations, minimization of dose causing a low signal-to-noise ratio (SNR), patient motion, registration, beam hardening, as well as other artifacts.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present invention may generally relate to techniques for processing dynamic image data sets. In one embodiment, a computer-implemented method includes receiving a set of dynamic computed tomography image data from an imaging system, registering the dynamic computed tomography image data, applying a smoothing filter to at least a selection of the set of the registered dynamic computed tomography image data, and outputting the results. The smoothing filter may be, for example, a uniform filter, a triangular filter, a Gaussian filter, a median or percentile filter, a Kuwahara filter, an anisotropic filter, or any combination thereof.

Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
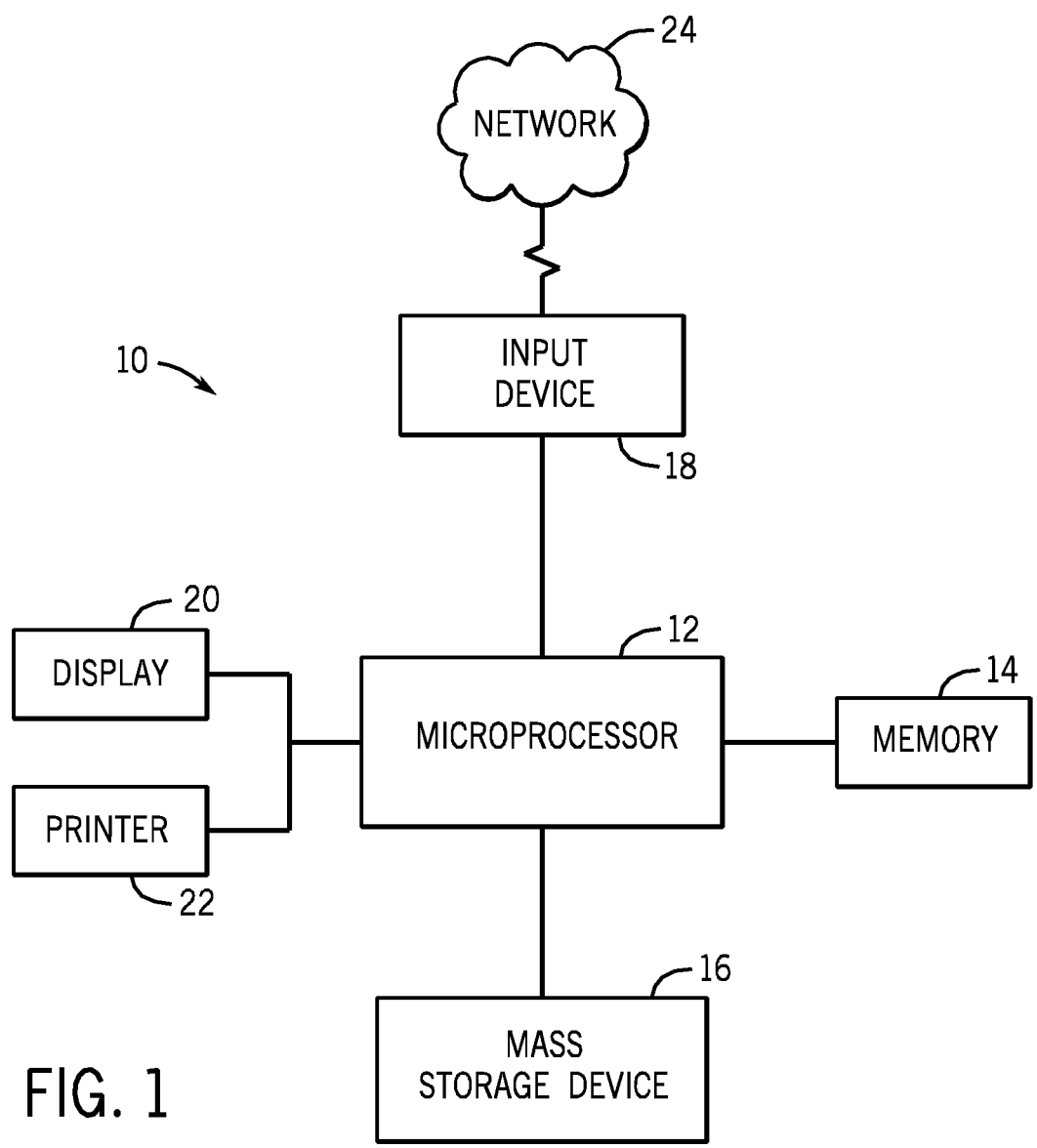
FIG. 1 is a block diagram of an exemplary processor-based device or system in accordance with one embodiment of the present invention.

Turning now to the drawings, and referring first to FIG. 1, an exemplary processor-based system 10 for use in conjunction with the techniques described herein is depicted. The exemplary processor-based system 10 may be a general-purpose computer, such as a personal computer, configured to run a variety of software, including software implementing all or part of the present technique. Alternatively, the processor-based system 10 may include, among other things, a mainframe computer, a distributed computing system, or an application-specific computer or workstation configured to implement all or part of the present technique based on specialized software and/or hardware provided as part of the system. Further, the processor-based system 10 may include either a single processor or a plurality of processors to facilitate implementation of the presently disclosed functionality.

In general, the exemplary processor-based system 10 may include a microcontroller or microprocessor 12, such as a central processing unit (CPU), which may execute various routines and processing functions of the system 10. For example, the microprocessor 12 may execute various operating system instructions as well as software routines configured to effect certain processes and stored in or provided by a manufacture including a computer readable-medium, such as a memory 14 (e.g., a random access memory (RAM) of a personal computer) or one or more mass storage devices 16 (e.g., an internal or external hard drive, a solid-state storage device, CD-ROM, DVD, or other storage device). In addition, the microprocessor 12 processes data provided as inputs for various routines or software programs, such as data provided as part of the present techniques in computer-based implementations.

Such data may be stored in, or provided by, the memory 14 or mass storage device 16. Alternatively, such data may be provided to the microprocessor 12 via one or more input devices 18. As appreciated by those of ordinary skill in the art, the input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network 24, such as a local area network or the Internet. Through such a network device, the system 10 may exchange data and communicate with other networked electronic systems, whether proximate to or remote from the system 10. It should be appreciated that the network 24 may include various components that facilitate communication, including switches, routers, servers or other computers, network adapters, communications cables, and so forth.

Results generated by the microprocessor 12, such as the results obtained by processing data in accordance with one or more stored routines of the present techniques, may be provided to an operator via one or more output devices, such as a display 20 and/or a printer 22. Based on the displayed or printed output, an operator may request additional or alternative processing or provide additional or alternative data, such as via the input device 18. As appreciated by those of ordinary skill in the art, communication between the various components of the processor-based system 10 may typically be accomplished via a chipset and one or more busses or interconnects which electrically connect the components of the system 10. Notably, in certain embodiments of the present technique, the exemplary processor-based system 10 may be configured to process image data sets acquired from any number of modalities, such as computed tomography (CT), positron emission tomography (PET), magnetic resonance (MR), and/or ultrasound, using one or more smoothing filters, as discussed below.

Figure 2:
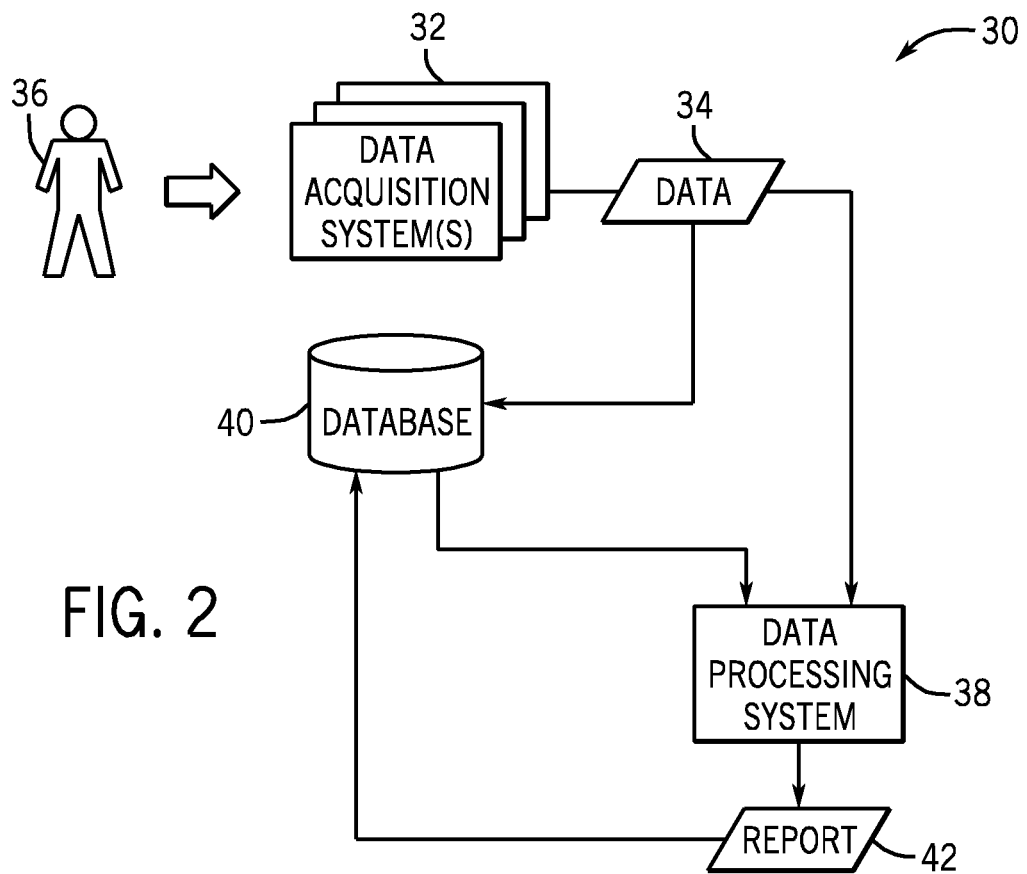
FIG. 2 is a block diagram generally depicting the operation of an exemplary system including a data acquisition system and a data processing system in accordance with one embodiment of the present invention.
Figure 3:
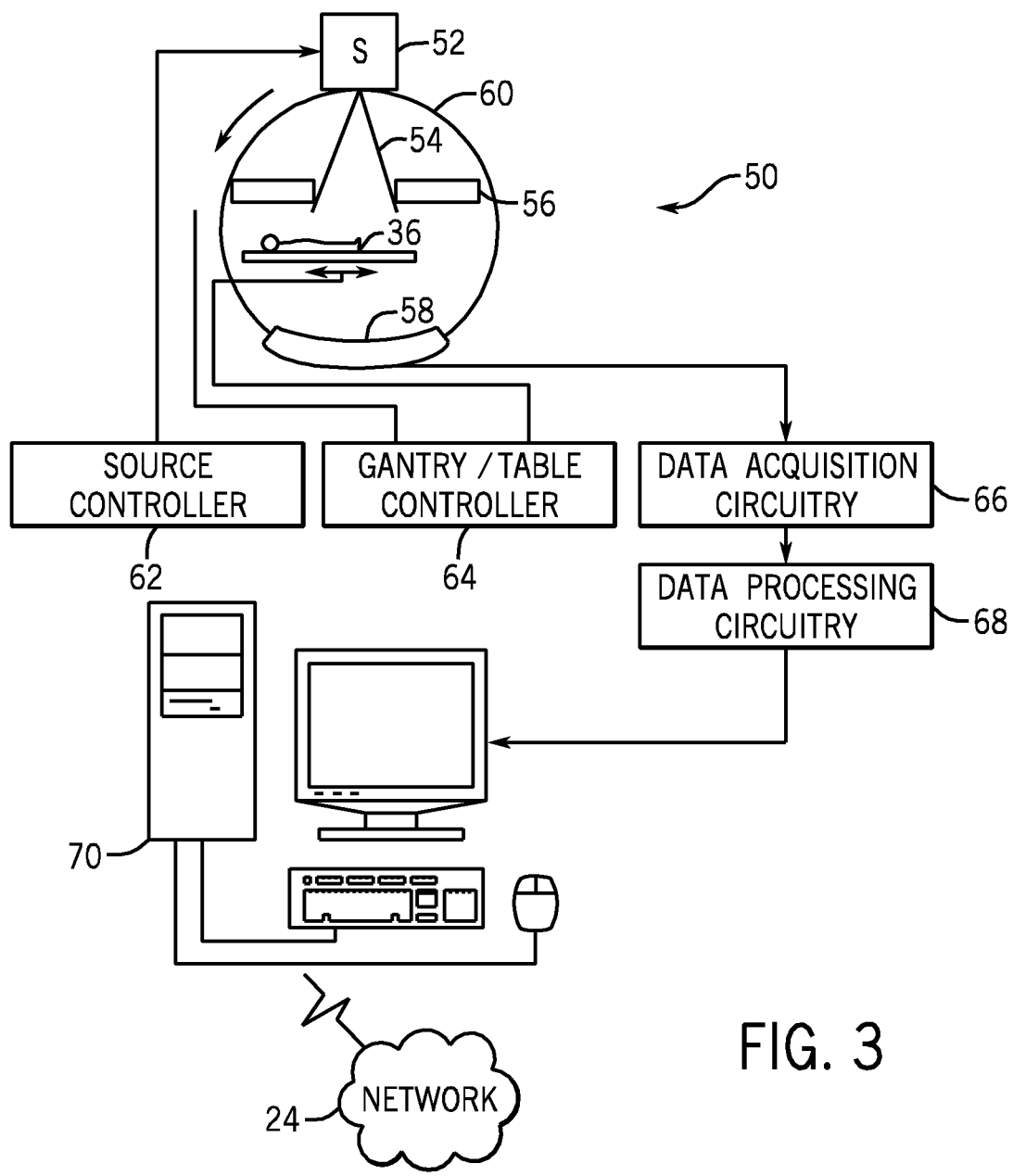
FIG. 3 is a diagrammatical representation of an exemplary computed tomography imaging system for use in accordance with one embodiment of the present invention.

An exemplary system 30 for acquiring and processing data in accordance with one embodiment of the present invention is illustrated in FIG. 2. The system 30 may include one or more data acquisition systems 32 that collect data 34 from, or regarding, a patient 36. The data 34 may include either or both of image data and non-image data, which may include, among other things, dynamic time-series image data sets acquired by any modality. Further, the data 34 may be received from static or dynamic data sources, including the data acquisition systems 32, and processed by a data processing system 38. The data processing system 38 may include the processor-based system 10 discussed above, or any other or additional components or systems that facilitate data processing in accordance with the presently disclosed technique.

It will be appreciated that the data 34 may be stored in a database 40, and that the data processing system 38 may receive the data 34 directly from the data acquisition systems 32, from the database 40, or in any other suitable fashion. Further, the data processing system 38 may also receive additional data from the database 40 for processing. As discussed in greater detail below, the processing performed by the data processing system 38 may include accessing the data 34, processing all or selected anatomical structures represented by the data 34 using a model-based temporal and/or spatial smoothing filter, and outputting some indication of the results, typically as visualized 4D dynamic CT data and generally indicated by the report 42 in FIG. 2. It should be noted that the data processing system 38 may be a processor-based system such as that illustrated in FIG. 1, and may include any suitable combination of hardware and/or software adapted to perform the presently disclosed functionality. Further, while certain embodiments of the present technique may be discussed with respect to medical data and devices, it is noted that the use of the present technique with non-medical data and systems is also envisaged.

While additional details of the operation of a data processing system 38 in accordance with certain embodiments are provided below, it is first noted that the presently disclosed techniques are applicable to data obtained from a wide array of data sources (e.g., data acquisition systems 32) that may provide time-series imaging data (e.g., CT perfusion data). In accordance with an embodiment, the data acquisition system 32 may be a CT imaging system 50. The CT imaging system 50 includes a radiation source 52 configured to generate X-ray radiation in a fan-shaped beam 54. A collimator 56 defines limits of the radiation beam. The radiation beam 54 is directed toward a curved detector 58 made up of an array of photodiodes and transistors which permit readout of charges of the diodes depleted by impact of the radiation from the source 52. The radiation source 52, the collimator 56 and the detector 58 are mounted on a rotating gantry 60 to enable them to be rapidly rotated (e.g., at speeds of two rotations per second).

During an examination sequence, as the source 52 and detector 58 are rotated, a series of view frames are generated at angularly-displaced locations around a patient 36 positioned within the gantry. A number of view frames (e.g. between 500 and 1000) are collected for each rotation, and a number of rotations may be made, such as in a helical pattern as the patient is slowly moved along the axial direction of the system. For each view frame, data is collected from individual pixel locations of the detector 58 to generate a large volume of discrete data. A source controller 62 regulates operation of the radiation source 52, while a gantry/table controller 64 regulates rotation of the gantry and control of movement of the patient.

Dynamic four-dimensional (4D) image data may be obtained using the CT imaging system 50 in a variety of ways. In one example, iodine contrast may be inserted into the bloodstream of the patient 36. View frame images acquired by the CT imaging system 50 may record a time at which each view frame image is acquired. Taken together, the series of view frame images may form a dynamic image data set that may be processed according to the techniques described herein.

Data collected by the detector is digitized and forwarded to data acquisition circuitry 66. The data acquisition circuitry 66 may perform initial processing of the data, such as for generation of a data file. The data file may incorporate other useful information, such as relating to cardiac cycles, positions within the system at specific times, and so forth. Data processing circuitry 68 then receives the data and performs a wide range of data manipulation and computations.

In general, data from the CT scanner can be reconstructed in a range of manners. For example, view frames for a full 360° of rotation may be used to construct an image of a slice or slab through the patient. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around the patient. Reconstruction of the data into useful images then includes computations of projections of radiation on the detector and identification of relative attenuations of the data by specific locations in the patient. The raw, the partially processed, and the fully processed data may be forwarded for post-processing, storage and image reconstruction. The data may be available immediately to an operator, such as at an operator interface 70, and may be transmitted remotely via a network connection 24.

While operations may be performed on the image data prior to viewing, the operator interface 70 may be useful for viewing reconstructed images based upon the image data collected. The images may also be stored in short or long term storage devices, for the present purposes generally considered as included within the interface 70. By way of example, the images may be transferred to a picture archiving communication systems (PACS) or a remote data processing system 38, via the network 24. It should also be noted that, from a general standpoint, the operator interface 70 affords control of the imaging system, typically through interface with the system control circuitry.

Figure 4:
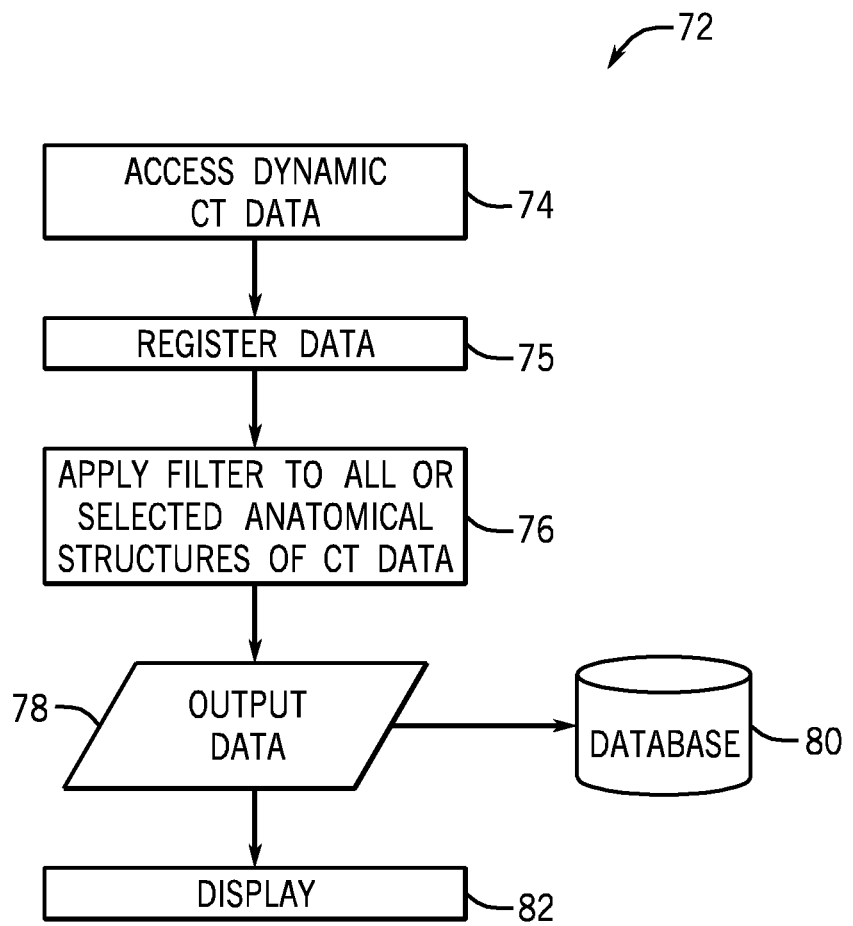
FIG. 4 is a flowchart of an exemplary data processing method provided in accordance with one embodiment of the present invention.

The remote data processing system 38 or a data processing system 38 associated with the operator interface 70, referred to generally as "the data processing system," may perform processing on any dynamic image data set that may be obtained from the CT imaging system 50 or from any imaging system of any other modality. Such data sets may include dynamic four-dimensional (4D) CT image data, which may represent images in three spatial dimensions and a time dimension, or three-dimensional (3D) image data, which may represent images in two spatial dimensions and a time dimension. Processing in the data processing system may generally include a technique illustrated by a flowchart 72, shown in FIG. 4. In a first step 74 of the flowchart 72, the data processing system may access a dynamic image data set. If the dynamic image data set is a dynamic (4D) CT data set, accessing the data set in step 74 may further include differentiating the type of the dynamic CT data set. For example, the data processing system may automatically ascertain whether the dynamic CT data set is Cine, Axial (Cine), Volume Shuttle, or Helical Shuttle data.

In step 75, a rigid model-based spatial (3D/3D) registration may be performed by the data processing system to register the dynamic tomographic data sets received in step 74. It should be appreciated that registration may be performed in the image space, but may also be performed in the data acquisition domain using the same coordinate systems for reliable rigid registration. Rigid registration methods that may be employed include, for example, landmark-based registration, segmentation-based registration, and/or voxel property-based registration.

Landmark-based registration may be based on a limited set of identified points, or landmarks, in the dynamic image data set. Among other things, the landmarks may be anatomical (i.e., salient and accurately locatable points of the morphology of the visible anatomy), or geometrical (i.e., points at the locus of the optimum of some geometric property). Because a set of identified landmarks may be sparse compared to the original dynamic image content, landmark-based registration may facilitate relatively fast optimization procedures. Such optimization procedures may be undertaken by the data processing system and may optimize measures of the landmark-based registration, which may be an average distance (L2 norm) between a landmark and a closest counterpart of the landmark, a Procrustean metric, or iterated minimal landmark distances. To compute or determine a Procrustean optimum, for example, the data processing system may rely on Arun's method, but may additionally or alternatively searched for using general optimization techniques. For the optimization of iterated minimal landmark distances, the data processing system may employ an iterative closest point ("ICP") algorithm and/or other derived methods. The data processing system may additionally or alternatively employ other methods of performing landmark registration, such as by testing a number of likely transformation hypotheses, which can, for example, be formulated by aligning three randomly selected points from each point set involved. Other common optimization methods may include quasi-exhaustive searches, graph matching, and dynamic programming methods.

Segmentation-based registration is an extension of landmark-based registration, and is based on the extraction of higher-order structures such as curves, surfaces, or volumes as landmarks. In the rigid model-based approach, anatomically identical structures may be extracted from image sets at different points in time to be registered, and used as a sole input for an alignment procedure. Although other registration models exist (e.g., deformable model or Chamfer matching technique), rigid model approaches tend to be popular methods in the clinical use in neuro-imaging.

Voxel property-based registration methods operate directly on gray values of the image data, without prior data reduction by a user or segmentation. These methods are generally subdivided into two distinct approaches. The first approach may reduce immediately the image gray value content to a representative set of scalars and orientations. The second approach may use all of the image data, or the full image content, throughout the registration process.

Principal axes and moment-based methods are examples of reductive registration methods. These methods may determine a center of gravity and a plurality of principal axis from moments of the image data, such as zeroth and first order moments of the image data. Registration may then be performed by aligning the center of gravity and the principal axes. In some cases, higher order moments may also be computed and used in the registration process. Moment-based methods can also use segmented or binarized image data as input. Voxel property based methods using the full image content may generally require minimum or no data reduction, but may use all of the available information throughout the registration process. Exemplary paradigms that can be used for full image content registration include cross-correlation, Fourier domain based cross-correlation, and phase-only correlation; minimization of variance of intensity ratios; minimization of variance of grey values within segments; minimization of the histogram entropy of difference images; histogram clustering and minimization of histogram dispersion; maximization of mutual information; maximization of zero crossings in difference images; cepstral echo filtering; determination of the optic flow field; and the like.

Whether landmark, segmentation, or voxel property based registration method is used during step 75, parameters that make up the registration may be typically determined through an optimization procedure. Exemplary optimization procedures include, but are not limited to, Powell's methods, the Downhill Simplex method, Brent's method and series of one-dimensional searches, Levenberg-Marquardt optimization, Newton-Raphson iteration, stochastic search methods, gradient descent methods, genetic methods, simulated annealing, geometric hashing, and quasi-exhaustive search methods. Frequent additions may be multi-resolution and multi-scale approaches to speed up convergence, to reduce the number of transformations to be examined, and to avoid local minima. For the rigid registration model, the ICP algorithm can also be useful.

In a next step 76, the data processing system may apply a smoothing filter to all or to a selection of the dynamic image data set, which may increase a signal-to-noise ratio (SNR) of the processed data and serve to accentuate structures of interest. If desired, the data processing system may first select one or more specific anatomical structures represented in the dynamic image data set before applying the filter. Such anatomical structures may include, for example, skeletal structures, vasculature, or soft tissue. By way of example, the data processing system may identify bony structures using a thresholding algorithm and/or may isolate the vasculature or soft tissue using Digital Subtraction Angiography, producing a data set of interest. It should be understood that the operator interface 70 may enable an operator to select the anatomical structure(s) of interest. Based on the selected anatomical structure and/or the type of the data (e.g., Cine, Axial (Cine), etc.), the data processing system may automatically select one or more optimal filters to apply to the data set of interest.

The one or more filters applied during step 76 may include any number of spatial and/or temporal filters, and may include one or more linear filters and/or one or more non-linear filters. Particularly, a linear filter applied to the dynamic image data set of interest may be, for example, a uniform filter, a triangular filter, and/or a Gaussian filter. A non-linear filter applied to the dynamic image data set of interest may be, for example, a median filter, a Kuwahara filter, or an anisotropic filter. Each of the above filters is described further below.

As noted above, a linear filter applied to the dynamic image data set may be a uniform filter. An output image resulting from application of the uniform filter may be based on a local averaging of the filter input (e.g., the images of the dynamic image data set of interest) in which all of the values within the filter support may have the same weight. It should be further appreciated that the uniform filter may be applied in either or both circular and rectangular implementations. The square implementation of the uniform filter may be separable and incremental, while the circular implementation may be merely incremental. Because the transfer functions of the circular and rectangular implementations of the uniform filter have negative lobes, application of a uniform filter may lead to phase reversal.

A triangular filter may represent another linear filter that may be applied to the dynamic image data set. An output image resulting from application of the triangular filter may be based on a local averaging of the filter input (e.g., the images of the dynamic image data set of interest) in which the values within the filter support have different weights. The triangular filter may be represented as the convolution of two uniform filters, which may be rectangular or circular. It should be appreciated that the transfer functions of triangular filters do not have negative lobes. As such, the application of the triangular filter to the dynamic image data set of interest would not cause phase reversal.

A Gaussian filter may represent a third form of linear filter that may be applied to the dynamic image data set. Several desirable characteristics may accompany the use of a Gaussian filter, such as its relation to the central limit theorem and minimum space-bandwidth product, as well as its applicability to edge detection and scale space analysis. Generally, the four-dimensional (4D) Gaussian filter is described by the following equation:

$$h(x, y, z, t) = \left(\frac{1}{\sqrt{2\pi}\sigma}e^{-(x^2/2\sigma^2)}\right) \cdot \left(\frac{1}{\sqrt{2\pi}\sigma}e^{-(y^2/2\sigma^2)}\right) \cdot \left(\frac{1}{\sqrt{2\pi}\sigma}e^{-(z^2/2\sigma^2)}\right) \cdot \left(\frac{1}{\sqrt{2\pi}\sigma}e^{-(t^2/2\sigma^2)}\right), \quad (1)$$

where x, y, and z represent three spatial dimensions, and t represents the fourth dimension, time. The Gaussian filter may be implemented with a variety of techniques, including using a finite number of samples $N_o$ of the Gaussian as the convolution kernel, repetitive convolution using a uniform filter as the convolution kernel, multiplication in the frequency domain, and recursive implementation.

As noted above, the temporal and/or spatial smoothing filter applied to the dynamic image data set may be a non-linear filter. One such non-linear filter may be represented by a median filter. To apply a median filter to the dynamic image data set of interest, a window may be moved across an image, and the median value of the CT density values within the window may be calculated. A given selected value may be exactly equal to one of the existing CT densities within the window, such that no round-off error may be present. Variations of the median filter, such as a percentile filter, may also be applied to the dynamic image data set. When a percentile filter is applied, the center voxel (volume element) within the window may be replaced by a p % CT density, rather than by the median value.

A Kuwahara filter may represent another non-linear smoothing filter that may be applied to the dynamic image data set. The Kuwahara filter is an edge-preserving filter, which may smooth the image data with a minimal disruption of sharpness and position of the edges, and may be implemented for a variety of shapes. The output of the Kuwahara filter may be assigned the mean value of a region within a window of interest having the lowest variance.

A third non-linear smoothing filter that may be applied to the dynamic image data set may be an anisotropic filter, which represents an iterative, "tunable" filter that encourages intraregional smoothing while inhibiting intraregional smoothing. A process for implementing the anisotropic filter may be represented according to the following equation:

$$\frac{\partial}{\partial t}I(\bar{x}, t) = \nabla \cdot (c(\bar{x}, t)\nabla I(\bar{x}, t)). \quad (2)$$

In Equation (2) above, $I(\bar{x},t)$ represents the 4D CT image data set and $c(\bar{x},t)$ represents a monotonically decreasing function (e.g., a diffusion function) of the image gradient magnitude. It should be appreciated that $\bar{x}$ corresponds to the three spatial dimensions (x, y, z) and t corresponds to time. Employing the diffusion function may permit locally adaptive diffusion strengths such that edges may be selectively smoothed or enhanced. As described, the discrete implementation of the non-linear anisotropic smoothing filter may be a numerical integration of a partial differential equation.

Following the application of the smoothing filter in step 76, the data processing system may output the smoothed dynamic image data set in an output step 78. The smoothed dynamic image data set may be stored in a local or remote database 80, such as within a storage medium of a PACS, the operator interface 70, or some other computer, or may be sent to a display 82. On the display 82, the smoothed dynamic image data set may show a wash-in and wash-out of contrast of anatomical structures of the dynamic image data set. By way of example, if the dynamic image data set included CT perfusion image data for the purpose of diagnosing acute stroke, the display 82 may show a wash-in and wash-out in the brain vasculature, which may enable the visualization of both arterial and venous phases. To further differentiate between the arterial and venous phases, the display 82 may display the arterial and venous phases in different colors. It should be appreciated that the dynamic visualization of the smoothed dynamic image data set may be in many possible forms, including that of a 4D virtual reality (VR) movie or a 4D thick slab Maximum Intensity Projection (MIP).

A technical effect of the subject matter described herein may include, among other things, improvement of dynamic image quality, which may facilitate diagnosis of various conditions. For certain conditions, such as stroke, the improvement of dynamic image quality may facilitate diagnosis using a single examination, such as a CT perfusion examination. The improvement of dynamic image quality may additionally alleviate imaging problems introduced by temporal sampling limitations, minimization of dose, patient motion, registration, beam hardening, or other artifacts. Moreover, while certain examples are generally discussed above with respect to particular devices or systems, such as CT, it will be appreciated that the present technique may also find applicability when used with other imaging modalities that may acquire dynamic image data.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
a memory device having a plurality of routines stored therein;
a processor configured to execute the plurality of routines stored in the memory device, the plurality of routines comprising:
a routine configured to effect, when executed, receiving a set of dynamic computed tomography image data from a computed tomography imaging system over the course of a single computed tomography perfusion examination from a data source;
a routine configured to effect, when executed, registration of the dynamic computed tomography image data;
a routine configured to effect, when executed, selection of a subset of the set of registered dynamic computed tomography image data using Digital Subtraction Angiography, wherein the subset corresponds to one or more anatomical features of a larger set of anatomical features, and wherein the one or more anatomical structures consist essentially of brain vasculature;
a routine configured to effect, when executed, application of a smoothing filter to substantially only the subset of the set of registered dynamic computed tomography image data; and
a routine configured to effect, when executed, output of the set of smoothed registered dynamic computed tomography image data for display showing wash-in and wash-out of the one or more anatomical features, wherein the output comprises showing wash-in and wash-out of the brain vasculature and showing arterial and venous phases in different colors.

2. The system of claim 1, wherein registration comprises landmark-based registration, segmentation-based registration, voxel property-based registration, principal axes or moment-based registration, or any combination thereof.

3. The system of claim 1, wherein the data source comprises a computed tomography imaging system configured to acquire image data pertaining to a patient.

4. The system of claim 1, wherein the data source comprises a database of dynamic computed tomography image information.

5. The system of claim 1, wherein the routine configured to effect, when executed, application of the smoothing filter is configured to effect application of a linear smoothing filter to substantially only the subset of the registered dynamic computed tomography image data.

6. The system of claim 5, wherein the linear smoothing filter applied to substantially only the subset of the registered dynamic computed tomography image data comprises a uniform filter, a triangular filter, a Gaussian filter, or any combination thereof.

7. The system of claim 1, wherein the routine configured to effect, when executed, application of the smoothing filter is configured to effect application of a non-linear smoothing filter to substantially only the subset of the registered dynamic computed tomography image data.

8. The system of claim 7, wherein the non-linear smoothing filter applied to substantially only the subset of the registered dynamic computed tomography image data comprises a median filter, a percentile filter, a Kuwahara filter, an anisotropic filter, or any combination thereof.

9. A computer-implemented method comprising:
using a processor of a data processing system to perform the steps of:
receiving a set of dynamic computed tomography image data from a computed tomography imaging system over the course of a single computed tomography perfusion examination;
registering the set of dynamic computed tomography image data;
choosing a subset of the set of registered dynamic computed tomography image data using Digital Subtraction Angiography, wherein the subset corresponds to one or more anatomical features of a larger set of anatomical features, and wherein the one or more anatomical structures consist essentially of brain vasculature;
applying a smoothing filter to substantially only the subset of the set of registered dynamic computed tomography image data; and
outputting the set of smoothed registered dynamic computed tomography image data for display showing wash-in and wash-out of the one or more anatomical features, wherein outputting comprises showing a wash-in or wash-out of the brain vasculature and showing arterial and venous phases in different colors.

10. The computer-implemented method of claim 9, wherein the smoothing filter applied to at least the subset of the set of registered dynamic computed tomography image data comprises a uniform filter, a triangular filter, a Gaussian filter, a median filter, a percentile filter, a Kuwahara filter, an anisotropic filter, or any combination thereof.

11. The computer-implemented method of claim 9, wherein outputting the results comprises displaying a dynamic visualization in the form of a four-dimensional virtual reality movie or a four-dimensional thick slab maximum intensity projection.

12. A system comprising:
   a memory device having a plurality of routines stored therein;
   a processor configured to execute the plurality of routines stored in the memory device, the plurality of routines comprising:
      a routine configured to effect, when executed, receiving of a dynamic computed tomography image data set obtained during a single computed tomography perfusion examination from a data source;
      a routine configured to effect, when executed, registration of the dynamic computed tomography image data set;
      a routine configured to effect, when executed, application of a smoothing filter to a subset of the registered dynamic computed tomography image data set; and
      a routine configured to effect, when executed, outputting of results of the application of the smoothing filter to the registered dynamic computed tomography image data set;
   wherein the routine configured to effect, when executed, application of the smoothing filter is configured to effect application of a four-dimensional Gaussian filter according to the following relationship:

$$h(x, y, z, t) = \left(\frac{1}{\sqrt{2\pi}\sigma}e^{-(x^2/2\sigma^2)}\right) \cdot \left(\frac{1}{\sqrt{2\pi}\sigma}e^{-(y^2/2\sigma^2)}\right) \cdot \left(\frac{1}{\sqrt{2\pi}\sigma}e^{-(z^2/2\sigma^2)}\right) \cdot \left(\frac{1}{\sqrt{2\pi}\sigma}e^{-(t^2/2\sigma^2)}\right),$$

where x, y, and z represent the three spatial dimensions and t represents time.

13. A system comprising:
   a memory device having a plurality of routines stored therein;
   a processor configured to execute the plurality of routines stored in the memory device, the plurality of routines comprising:
      a routine configured to effect, when executed, receiving of a dynamic computed tomography image data set obtained during a single computed tomography perfusion examination from a data source;
      a routine configured to effect, when executed, registration of the dynamic computed tomography image data set;
      a routine configured to effect, when executed, application of a smoothing filter to a subset of the registered dynamic computed tomography image data set; and
      a routine configured to effect, when executed, outputting of results of the application of the smoothing filter to the registered dynamic computed tomography image data set;
   wherein the routine configured to effect, when executed, application of the smoothing filter is configured to effect application of anisotropic filter according to the following relationship:

$$\frac{\partial}{\partial t}I(\bar{x}, t) = \nabla \cdot (c(\bar{x}, t)\nabla I(\bar{x}, t)),$$

where $I(\bar{x},t)$ represents the registered dynamic computed tomography image data, $c(\bar{x},t)$ represents a monotonically decreasing function, $\bar{x}$ corresponds to the three spatial dimensions, and t corresponds to time.

* * * * *